United States Patent [19]
Parikh et al.

[11] Patent Number: 6,123,926
[45] Date of Patent: Sep. 26, 2000

[54] SILICA CONTAINING DENTIFRICE COMPOSITIONS

[75] Inventors: Rita M. Parikh, Paramus; Charles W. Pozzi, Fanwood; Nuray Asral, Rockaway; Bruce Kohut, Toms River, all of N.J.

[73] Assignee: Warner-Lambert Company, Morris Plains, N.J.

[21] Appl. No.: 09/290,620

[22] Filed: Apr. 13, 1999

[51] Int. Cl.[7] .............................. A61K 7/16; A61K 7/18; A61K 33/16

[52] U.S. Cl. .............................. 424/52; 424/49; 424/673; 424/676

[58] Field of Search ........................... 424/49–58

[56] References Cited

U.S. PATENT DOCUMENTS

| | | |
|---|---|---|
| 1,526,940 | 2/1925 | Staegemann et al. . |
| 3,164,524 | 1/1965 | Fand et al. . |
| 4,545,979 | 10/1985 | Ambike et al. . |
| 4,550,018 | 10/1985 | Ambike et al. . |
| 5,094,843 | 3/1992 | Mazzanobile et al. . |
| 5,234,673 | 8/1993 | McGill et al. ........................... 423/338 |
| 5,419,888 | 5/1995 | McGill et al. ........................... 423/338 |
| 5,647,903 | 7/1997 | McGill et al. ........................... 426/49 |

FOREIGN PATENT DOCUMENTS

| | | |
|---|---|---|
| 834131 | 2/1970 | Canada . |
| 0497476 | 8/1992 | European Pat. Off. . |
| WO9603109 | 2/1996 | WIPO . |

OTHER PUBLICATIONS

Prencipe, et al.; "Squeezing out a better toothpaste". Chemtech, Dec. 1995; pp. 38–42.

Wasay, et al.; "Adsorption of fluoride, phosphate, and arsenate ions on lanthanum–impregnated silica gel". Water Environment Research, vol. 68, No. 3, May/Jun. 1996, pp. 295–300.

Sloane; "Dentifrices". Henley's Twentieth Century Book of Formulas, Processes and Trade Secrets, 1965, pp. 251–253.

*Primary Examiner*—Shep K. Rose
*Attorney, Agent, or Firm*—Evan J. Federman

[57] ABSTRACT

The level of fluoride ions in a sodium fluoride containing low pH dentifrice remains stable when the silica has a moisture content of less than about 11% by weight of the silica.

9 Claims, No Drawings

SILICA CONTAINING DENTIFRICE COMPOSITIONS

BACKGROUND OF THE INVENTION

1. Field of the Invention

The present invention relates to silica containing dentifrice compositions. Specifically, the invention is directed to a dentifrice composition with sodium fluoride having a low pH wherein the silica has a specific moisture content.

2. Description of Related Art

Low pH dentifrice compositions that contain abrasive silica are known in the art. Specifically, PCT Application WO 96/03109 to Warner-Lambert Company teaches an antiseptic, anticaries dentifrice having a pH of about 3.0 to about 5.5. The silicas used in the dentifrice include ZEODENT® 113 and SYLODENT® 750. The fluoride can be sodium monofluorophosphate, sodium fluoride and stannous fluoride.

U.S. Pat. Nos. 4,545,979 and 4,550,018 to Ambike et al. teach a dental hygiene composition in an acidic pH range of from 3.0 to 5.0. The fluorides used are sodium monofluorophosphate, sodium fluoride and stannous fluoride. The silica is ZEODENT® 113.

U.S. Pat. No. 5,094,843 to Mazzanobile et al. teaches an anti-plaque, anti-gingivitis toothpaste with a fluoride source and an antimicrobial agent consisting essentially of about 0.15% to about 0.80% thymol, about 0.15% to about 1.00% methyl salicylate, about 0.25% to about 0.80% eucalyptol and from about 0.15% to about 0.60% menthol. Mazzanobile et al. teach that the toothpaste will usually have a pH of from about 4 to about 8. The only example in Mazzanobile et al. has a pH of about 6.3. Mazzanobile et al. also disclose that Euthymol toothpaste has been sold in the United Kingdom. According to Mazzanobile et al. Euthymol toothpaste contains 0.12% thymol, 1.26% methyl salicylate, 0.07% menthol and 0.012% eucalyptol. Euthymol toothpaste has a pH of approximately 7.3–7.5. The fluorides taught in Mazzanobile include alkali metal fluoride, preferably sodium fluoride. The abrasives are generally described as silica dental abrasives such as those marketed under the tradenames "Zeodent" and "Slyodent."

Canadian Patent No. 834131 to Tisserand teaches a dentifrice preparation that has an acidic pH of about 3.8 to 5.8, optimally a pH of 4.0 to 5.5, and most preferably a pH of 4.0 to 4.8. Tisserand teaches using numerous fluoride sources including sodium fluoride. The abrasives are described as polishing agents including aluminum silicate and zirconium silicate.

The problem of poor stability of fluoride in silica containing, low pH dentifrice compositions is also known. For example, Prencipe et al., "Squeezing Out A Better Toothpaste", *Chemtech,* Dec. 5, 1995, pp. 38–42, teaches that sodium fluoride can be trapped by the silica at pH values significantly<7.

U.S. Pat. No. 4,350,583 to Wason teaches a silica composition for use in a toothpaste that is highly compatible with fluoride, including sodium fluoride. The toothpaste has a pH of from about 4 to 8 when slurried with water in a 3:1 water/composition weight ratio.

While the prior art discloses toothpaste and other dentifrice compositions with silica and sodium fluoride at low pH, there is a need for dentifrice compositions wherein the silica is chosen to so as maximize the available fluoride.

SUMMARY OF THE INVENTION

The present invention is directed to a dentifrice composition comprising sodium fluoride and a silica having a moisture content of less than about 11%.

More particularly, the present invention is directed to dentifrice compositions that have sodium fluoride and a precipitated silica having a moisture content of about 4 to about 11% by weight of the silica.

DETAILED DESCRIPTION OF PREFERRED EMBODIMENTS

The compositions according to the present invention contain a silica having less than 11% moisture. The silica can be any type of silica including those known as abrasive silicas and gelling silicas. Examples of currently commercially available silicas that contain less than about 11% moisture include ZEODENT® 165, 200 and 113, available from the J. M. Huber Company, SYLODENT® 2, 15, 700 and 704, available from the W. R. Grace Corp., HiSil® DA 267 and DA 105-T, available from PPG Ind. and SIDENT® 8, 9, 10 and 22S, available from Degussa Co.

The amount of silica present in the compositions ranges from about 1 to about 50 percent by weight, preferably about 5 to about 30 percent by weight and even more preferably about 7 to about 22 percent by weight.

The compositions according to the present invention include sodium fluoride as the fluoride source. The amount of sodium fluoride compound present in the dentifrice compositions of this invention is in an amount by weight of up to about 1.2% w/w, preferably from about 0.1% w/w to about 0.5% w/w, and most preferably from about 0.175% w/w to about 0.33% w/w of the dentifrice composition so as to provide 800–1500 ppm $F^-$.

The pH of the compositions according to the present invention is from about 4.0 to about 5.0. The pH of the claimed dentifrice is adjusted to below 5.0 using suitable food or pharmaceutical grade acidifiers. These include, but are not limited to, one or a combination of the following: phosphoric acid, benzoic acid, citric acid, or other tricarboxylic acids, and the like. Acidifiers in the present invention include a mixture of phosphoric acid from about 0.01% w/w to about 3.0% w/w, preferably in the range of from about 0.1% w/w to about 1.5% w/w, and most preferably in the range of from about 0.2% w/w to about 0.75% w/w; monobasic sodium phosphate from about 0.01% w/w to about 1% w/w, preferably from about 0.1% w/w to about 0.5% w/w and most preferably from about 0.2% w/w to about 0.4% w/w; dibasic sodium phosphate from about 0.001% w/w to about 1.0% w/w, preferably from about 0.01% w/w to about 0.5% w/w and most preferably from about 0.01% w/w to about 0.05% w/w; and benzoic acid in the range of from about 0.01% w/w to about 1.0% w/w, preferably from about 0.05% w/w to about 0.5% w/w, and most preferably from about 0.08% w/w to about 0.35% w/w. The exact amount of acidifier added will depend on the final pH and buffer capacity desired.

The pH of the products may be buffered with salts of the acids in question. Common buffer systems include phosphoric acid and sodium phosphate salts, or citric acid and sodium citrate. Suitable buffers for use in this invention include citric acid-sodium citrate, phosphoric acid-sodium phosphate, sodium monobasic phosphate-sodium dibasic phosphate, acetic acid-sodium acetate, gluconic acid-sodium gluconate and benzoic acid and sodium benzoate in amounts up to about 1% w/w, preferably from about 0.05% w/w to about 0.75% w/w of the composition and most preferably from about 0.1% w/w to about 0.5% w/w of the composition.

The compositions of the present invention may also contain conventional dentifrice additives including, but not limited to, humectants, binders, thickeners, surfactants, preservatives, sweeteners, flavors, colors, glycerin, and a buffer. These additives are present in amounts that do not interfere with the antiseptic, antigingivitis and anticaries properties of the composition of the present invention.

Surfactants or surface active agents are organic compounds that reduce surface tension between liquids and aid in the dispersion of a composition throughout the oral cavity. The surfactant in the present invention may be anionic, nonionic, or amphoteric. The oral hygiene or dentifrice compositions of the present invention may contain surfactants in amounts up to about 5.0% w/w; preferably from about 0.1% w/w to about 3.0% w/w of the dentifrice composition; and most preferably from about 0.2% w/w to about 2.0% w/w of the dentifrice composition.

The most preferred surfactants are anionic. These anionic surfactants include, but are not limited to, sodium lauryl sulfate, sodium lauroyl sarcosinate, sodium methyl cocoyl taurate, and disodium lauryl sulfosuccinate. A preferred surfactant is sodium lauryl sulfate. The compositions according to the present invention are substantially free from one or more highly pure alkali metal salts of dodecyl sulphate having less than 5% non-dodecyl alkyl sulphate salts.

Amphoteric surfactants have the capacity to behave as either an acid or a base and include quaternized imidazole derivatives. Preferred amphoteric surfactants include long chain (alkyl) amino-alkylene aklylated amine derivatives, also known as MIRANOL®, manufactured by Rhone-Poulanc, Cranberry, N.J.

Natural and artificial sweeteners may be used in the dentifrice compositions. The sweetener may be selected from a wide range of well known materials including naturally occurring water-soluble sweeteners, artificial water-soluble sweeteners and modified water-soluble sweeteners derived from naturally occurring water-soluble sweeteners. Artificial water-soluble sweeteners include, but are not limited to, soluble saccharin salts, e.g., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin and dipeptide based sweeteners, such as L-aspartic acid derived sweeteners. Dipeptide sweeteners include L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenylglycine, L-aspartyl-2,5-dihydro-L-phenylalanine and L-aspartyl-L-(1-cyclohexene)-alanine. Naturally occurring water-soluble sweeteners include, but are not limited to, sugar alcohols, including sorbitol as 70% sorbitol solution, mannitol, xylitol, maltitol, hydro-genated starch hydrolysates and mixtures thereof.

Water-soluble sweeteners derived from naturally occurring water-soluble sweeteners include, but are not limited to, chlorinated derivatives of sucrose, known, for example, under the product designation of Sucralose; and protein-based sweeteners such as *thaumaoccous danielli* (Thaumatin I and II).

Sorbitol solution supplies sweetness and body to the composition and gives a desirable mouth feel. Sorbitol solution also enhances flavor, prevents harsh taste and provides a fresh and lively sensation in the mouth. It also prevents caking of the dentifrice.

In general, an effective amount of sweetener is utilized to provide the level of sweetness desired in any particular embodiment of the dentifrice compositions according to the present invention. This amount will vary with the sweetener selected and the final form of the composition. The amount of sweetener normally present is from about 0.0025% w/w to about 60% w/w of the dentifrice composition. The exact range of amounts for each type of sweetener in a dentifrice is readily determined by those skill in the art.

The dentifrice compositions of the present invention may include antimicrobial agents such as essential oils. These essential oils include, but are not limited to, thymol, menthol, methyl salicylate (wintergreen oil) and eucalyptol. Thymol, also known by the chemical formula 5-methyl 2-(1-methylethyl) phenol, is obtained from the essential oil of *Thymus vulgaris Labiatae* and *Monarda punctata Labiatae*. Thymol is a white crystalline powder with an aromatic odor and taste. Thymol is soluble in organic solvents but only slightly soluble in deionized water.

Menthol is isolated principally from the oil of *Mentha arvensis*. In its commercial form, menthol is available as L-menthol crystals obtained from a process involving cooling of the oil. Fractional distillation of peppermint oil that usually contains from about 40% to about 65% menthol represents another important source of menthol. Synthetic sources of L-menthol are also available.

Eucalyptol is derived from the eucalyptus tree. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels.

Methyl salicylate is the main ingredient in many essential oils, constituting about 99% of oil of wintergreen (*Gaultheria procumbens*) and sweet birch (*Betula lenta*). Methyl salicylate, which has a distinctive refreshing aroma, is used widely in mouthwashes, chewing gums and other oral and pharmaceutical preparations.

Thymol may be in the dentifrice composition of this invention in an amount of from about 0.01% w/w to about 1.0% w/w; preferably in an amount of from about 0.1% w/w to about 0.6% w/w; and most preferably in an amount of from about 0.2% w/w to about 0.5% w/w.

Menthol may be in the dentifrice composition of the present invention in an amount of from about 0.01% w/w to about 1.0% w/w; preferably in an amount of from about 0.10% w/w to about 0.7% w/w; and most preferably in an amount of from about 0.1% w/w to about 0.6% w/w.

Eucalyptol may be in the dentifrice composition of the present invention in an amount of from about 0.01% w/w to about 1.5% w/w; preferably in an amount of from 0.1% w/w to about 1.0% w/w; and most preferably in an amount of from about 0.12% w/w to about 0.8% w/w.

Methyl salicylate may be in the dentifrice composition of the present invention in an amount of from about 0.01% w/w to about 1.0% w/w; preferably in an amount of from about 0.04% w/w to about 0.6% w/w; and most preferably in an amount of from about 0.1% w/w to about 0.6% w/w.

Even more specifically, the dentifrice compositions according to the present invention can include about 0.46% to about 0.56% thymol, about 0.43% to about 0.53% methyl salicylate, about 0.31% to about 0.37% menthol and about 0.67% to about 0.81% eucalyptol. Even more preferably a dentifrice according to the present invention contains about 0.51% thymol, about 0.51% methyl salicylate, about 0.34% menthol and about 0.77% eucalyptol.

While the specific examples set forth include essential oils as the antimicrobial agent, the present invention is not limited to any particular antimicrobial agent. Other antimicrobial agents that can be used in the present invention include triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European patent application Ser. No. 0,251,591 of Beecham Group, PLC, published Jan. 7, 1988; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpy chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and peroxides, such as sodium peroxide, hydrogen peroxide, and magnesium monoperphalate and its analogs as described in U.S. Pat. No. 4,670,252; and analogs and salts of the above antimicrobial agents. If present, the antimicrobial agents generally comprise from about 0.1% to about 5% by weight of the compositions of the subject invention.

The flavors that may be used in the invention include natural and artificial flavors known in the dentifrice art. Suitable flavors include, but are not limited to, mints, such as peppermint, citrus flavors such as orange and lemon, artificial vanilla, cinnamon, various fruit flavors, and the like. Anethole (or anise camphor, p-propenyl anisole) is a flavor constituent of anise and fennel oils that are used widely as flavoring agent and antiseptic and was found useful in masking the harsh taste of thymol.

The amount of flavor is normally a matter of preference subject to the type of final dentifrice composition, the individual flavor employed and the strength of flavor desired. The flavors are preferably utilized in amounts that may range from about 0.01% w/w to about 6% w/w of the dentifrice composition. The flavors used in the compositions according to the present invention are comprise flavoring oils that are not substantially free of terpenes.

Coloring agents are used in amounts effective to produce a dentifrice of the desired color. These coloring agents may be incorporated in amounts up to about 3% by weight of the dentifrice composition. The coloring agents may also include natural food colors and dyes suitable for food, drug and cosmetic applications. These coloring agents are known as FD & C dyes and lakes. The coloring materials are preferably water-soluble. Illustrative nonlimiting examples include the indigoid dye known as FD & C Blue No. 1, and D & C Yellow No. 10. A full recitation of all FD & C colorants and their corresponding chemical structures may be found in the Kirk-Othmer Encyclopedia of Chemical Technology, 3rd Edition, in volume 5 at pages 857–884. A preferred opacifier, titanium dioxide, may be incorporated in amounts up to about 2.0% w/w, preferably less than about 1.0% w/w of the composition and most preferably less than about 0.4% w/w.

Suitable humectants in this invention include sorbitol, as 70% sorbitol solution, glycerin, propylene glycol, polyethylene glycol, mixtures thereof, and the like. Humectants may be present in amounts from about 1.0% to about 75.0% by weight of the dentifrice composition.

The dentifrice composition includes an oral vehicle that can be a paste, gel, powder or liquid. Depending upon the specific form of the dentifrice, the composition may also include binders or gelling agents to provide a desired consistency. Gelling agents, in addition to the gelling silica, such as hydroxyethyl cellulose, carboxymethyl cellulose, methyl cellulose, xanthan gum and the like may be used singly or in combination. The preferred gelling system is a mixture of carboxy methyl cellulose, xanthan gum and gelling silica. Gelling agents may be used in amounts from about 0.5% w/w to about 30% w/w, preferably from about 10.0% w/w to about 20.0% w/w of the dentifrice composition, and most preferably from about 7.0% w/w to about 15% w/w of the composition.

The dentifrice composition of this invention may also contain a desensitizing agent such as strontium chloride, potassium nitrate or sodium citrate-citric acid, which may be used in an amount from about 0.5% w/w to about 10% w/w.

Suitable preservatives include benzoic acid, butylated hydroxyanisole (BHA), butylated hydroxytoluene (BHT), ascorbic acid, methyl paraben, propyl paraben, tocopherols and mixtures thereof. Preservatives when used are generally present in amounts up to about 1.0% w/w, and preferably from about 0.1% w/w to about 1.0% w/w of the dental gel composition.

The present invention is further illustrated by the following non-limiting examples. All parts and percentages in the examples and throughout the specification and claims are by weight of the final composition unless otherwise specified.

EXAMPLES 1–3

Examples 1–3 are dentifrice compositions. Each of the examples includes a silica or combination of silicas that are precipitated silicas. The ingredients are mixed using techniques known in the art.

COMPARATIVE EXAMPLES 1–2

Comparative Examples 1–2 are dentifrice compositions that include a silica gel. The ingredients are mixed using techniques known in the art. The formulas for Examples 1–3 and Comparative Examples 1–2 are summarized in Table 1.

Fluoride Stability

The amount of available fluoride in each of Examples 1–3 and Comparative Examples 1–2 were measured. Each of the toothpastes included 0.254 wt % of sodium fluoride, which is sufficient to provide 1100 ppm of fluoride ion after manufacturing losses.

Comparative Examples 1–2 had an initial fluoride ion amount of 667 ppm and 672 ppm, respectively. Examples 1–3 had an initial fluoride ion amount of 905–918 ppm. The amount of fluoride in the examples remained between 827–893 ppm after 12 weeks at 40° C. The fluoride stability results are summarized in Table 2.

An additional benefit of the present invention is the stability of the pH. As shown in Table 2, the pH of the comparative examples was significantly higher after 12 weeks at 40° C. then the pH of Examples 1–3.

TABLE 1

| Ingredient | Example 1 | Example 2 | Example 3 | Comparative Example 1 | Comparative Example 2 |
|---|---|---|---|---|---|
| Water, purified | 22.85930 | 718.85930 | 22.85930 | 22.85930 | 22.85930 |
| Sorbitol 70% | 40.0000 | 40.0000 | 40.0000 | 40.0000 | 40.0000 |
| Sodium fluoride | 0.25400 | 0.25400 | 0.25400 | 0.25400 | 0.25400 |
| Sodium Saccharin 851% | 1.20000 | 1.20000 | 1.20000 | 1.20000 | 1.20000 |
| $NaH_2PO_4$ (mono) | 0.29000 | 0.29000 | 0.29000 | 0.29000 | 0.29000 |
| $NaH_2PO_4$ (dibasic) | 0.03000 | 0.03000 | 0.03000 | 0.03000 | 0.03000 |
| Phosphoric acid 25% | 1.30000 | 1.30000 | 1.30000 | 1.30000 | 1.30000 |
| PEG 1450 | 3.00000 | 3.00000 | 3.00000 | 3.00000 | 3.00000 |
| Benzoic Acid | 0.15000 | 0.15000 | 0.15000 | 0.15000 | 0.15000 |
| FD + C Blue #1 .2% | 1.00000 | 1.00000 | 1.00000 | 1.00000 | 1.00000 |
| D&C Yellow #10 .1% | 0.25000 | 0.25000 | 0.25000 | 0.25000 | 0.25000 |
| Zeodent 113 | 18.00000 | 15.00000 | 0 | 0 | 0 |
| Zeosyl 165 | 0 | 7.0000 | 7.00000 | 7.00000 | 0 |
| Zeosyl 200 | 0 | 0 | 0 | 0 | 7.00000 |
| Degussa Sident 10 | 0 | 0 | 11.00000 | 0 | 0 |
| Sylodent 750 | 0 | 0 | 0 | 11.00000 | 11.00000 |
| Titanium dioxide | 0.35000 | 0.35000 | 0.35000 | 0.35000 | 0.35000 |
| Xanthan | 0.25000 | 0.25000 | 0.25000 | 0.25000 | 0.25000 |
| CMC7MF | 1.20000 | 1.20000 | 1.20000 | 1.20000 | 1.20000 |
| Glycerin | 6.00000 | 6.00000 | 6.00000 | 6.00000 | 6.00000 |
| Thymol | 0.51120 | 0.51120 | 0.51120 | 0.51120 | 0.51120 |
| Methyl Salicylate | 0.51600 | 0.51600 | 0.51600 | 0.51600 | 0.51600 |
| Menthol | 0.34000 | 0.34000 | 0.34000 | 0.34000 | 0.34000 |
| Eucalyptol | 0.77450 | 0.77450 | 0.77450 | 0.77450 | 0.77450 |
| Spearmint Oil 801A075 | 0.10000 | 0.10000 | 0.10000 | 0.10000 | 0.10000 |
| Mint flavor | 0.12500 | 0.12500 | 0.12500 | 0.12500 | 0.12500 |
| Sodium lauryl sulfate | 1.50000 | 1.50000 | 1.50000 | 1.50000 | 1.50000 |
| TOTAL | 100.00000 | 100.00000 | 100.00000 | 100.00000 | 100.00000 |

TABLE 2

| | Example 1 | Example 2 | Example 3 | Comparative Example 1 | Comparative Example 2 |
|---|---|---|---|---|---|
| pH | | | | | |
| Initial | 4.5 | 4.43 | 4.43 | 4.44 | 4.6 |
| 1 Week | 4.5 | 4.49 | 4.48 | 4.42 | 4.76 |
| 12 Weeks 40° C. | 4.46 | 4.51 | 4.49 | 5.2 | 5.15 |
| Available F | | | | | |
| Initial | 916 | 905 | 918 | 667 | 675 |
| 2 week 40° C. | 901 | 853 | 851 | — | 483 |
| 4 week 40° C. | 865 | 834 | 821 | | 460 |
| 12 week 40° C. | 893 | 827 | 859 | | 389 |

While the invention has been described in detail and with reference to specific examples thereof, it will be apparent to one skilled in the art that various changes and modifications can be made therein without departing from the spirit and scope thereof.b

What is claimed is:

1. A dentifrice composition comprising:
    a silica having a moisture content of less than 11% by weight of the silica,
    0.1 percent to 0.5 percent by weight sodium fluoride, and
    an oral vehicle; wherein the dentifrice has a pH of 4.0 to 5.0 and a fluoride availability greater than 90 percent after 12 weeks.
2. The dentifrice composition according to claim 1, wherein the silica is present in an amount from 1.0 to 50.0 percent by weight.
3. The dentifrice composition according to claim 2, wherein the silica is present in an amount from 5.0 to 30.0 percent by weight.
4. The dentifrice composition according to claim 3, wherein the silica is present in an amount from 7.0 to 22.0 percent by weight.
5. The dentifrice composition according to claim 1, wherein the sodium fluoride is present in an amount from 0.175% w/w to 0.33% w/w.
6. The dentifrice composition according to claim 1 wherein the silica is precipitated silica.
7. The dentifrice composition according to claim 1 wherein the moisture content of the silica is 4 to 11% by weight of the silica.
8. The dentifrice composition according to claim 7, wherein the silica is precipitated silica.
9. A dentifrice composition comprising:
    7.0 to 22 percent by weight of a precipitated silica having a moisture content of 4 to 11% by weight of the silica,
    0.175% w/w to about 0.33% sodium fluoride, and
    an oral vehicle; wherein the dentifrice has a pH of 4.0 to 5.0, and the amount of fluoride ions remains stable after 12 weeks at 40° C.

* * * * *